United States Patent [19]

Vanlerberghe et al.

[11] 4,425,364

[45] Jan. 10, 1984

[54] COMPOSITIONS CONTAINING AN ORGANO-SILICON COMPOUND

[75] Inventors: Guy Vanlerberghe, Commune de Villevaude; Henri Sebag, Paris, both of France

[73] Assignee: Societe Anonyme dite: L'Oreal, Paris, France

[21] Appl. No.: 83,515

[22] Filed: Oct. 10, 1979

Related U.S. Application Data

[63] Continuation-in-part of Ser. No. 918,963, Jun. 23, 1978, abandoned, which is a continuation of Ser. No. 763,699, Jan. 28, 1977, abandoned.

[30] Foreign Application Priority Data

Feb. 2, 1976 [FR] France ........................... 76 02787

[51] Int. Cl.³ .................. A61K 47/00; A61K 31/695; A61K 31/00
[52] U.S. Cl. ..................... 424/358; 424/64; 424/70; 424/59; 424/63; 424/168; 424/170; 424/184
[58] Field of Search .............. 424/168, 184, 170, 358, 424/365, 64, 70, 59, 63

[56] References Cited

U.S. PATENT DOCUMENTS

| | | | |
|---|---|---|---|
| 2,727,846 | 12/1965 | Talbot | 424/184 |
| 3,185,627 | 5/1965 | Kass | 424/358 |
| 3,641,239 | 2/1972 | Mohrlok | 424/64 |

FOREIGN PATENT DOCUMENTS

| | | | |
|---|---|---|---|
| 677857 | 1/1964 | Canada | 424/184 |
| 1179743 | 5/1959 | France | 424/358 |

*Primary Examiner*—Frederick E. Waddell

*Attorney, Agent, or Firm*—Cushman, Darby & Cushman

[57] ABSTRACT

A cosmetic of pharmaceutical composition containing an oily phase has as the said oily phase one comprising at least one organo-silicon compound of the formula

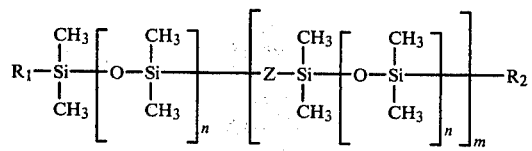

wherein $R_1$ and $R_2$ each independently represent a saturated linear alkyl containing 8–16 carbon atoms; Z represents

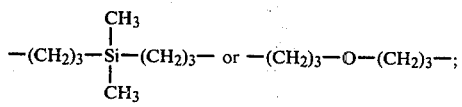

and m and n each equal 0 or 1. The organo-silicon compound can be present in the composition in an amount ranging from 1 to 100 percent by weight based on the total weight of the composition. When cosmetic or pharmaceutical active components are present in the composition, they are homogeneously distributed therein and such compositions have excellent spreading and feel characteristics. The compositions are usefully employed in topically applied formulations such as milks, creams, oils and lotions.

24 Claims, No Drawings

COMPOSITIONS CONTAINING AN ORGANO-SILICON COMPOUND

This application is a continuation-in-part of our application Ser. No. 918,963 filed June 23, 1978, now abandoned, which is a continuation of our application Ser. No. 763,699, filed Jan. 28, 1977, now abandoned.

The present invention relates to cosmetic or pharmaceutical compositions containing an "oily phase" which comprises certain organo-silicon compounds. By "oily phase" is meant, hereafter, in the general acceptation of the term, a fatty phase which is liquid or not at ambient temperature.

The use of silicon derivatives, particularly polymethylsiloxanes, in pharmaceutical or cosmetic compositions such as lotions, creams, lip rouges, hair lacquers and the like is known.

These silicon derivatives are generally employed in relatively weak concentrations, to facilitate spreading the composition on the skin or to avoid foam formation or to take advantage of their water repelling properties.

However, these silicon derivatives have often been found to be inconvenient, especially since they cannot be used in significant amounts. Thus their use as a principal or only component in the oily phase of such compositions has been discouraged because of the difficulty of emulsifying them, or because of their limited compatibility with conventional fatty bodies and emulsifying agents, or because of their disagreeable feel or touch.

The present invention which overcomes these drawbacks relates to a composition whose oily phase comprises, totally or partially, at least one organo-silicon compound of the formula

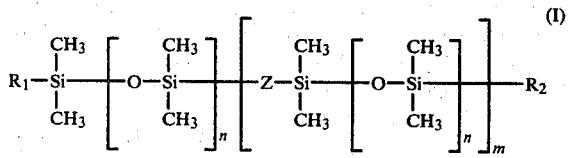

wherein
$R_1$ and $R_2$ each independently represent a saturated linear alkyl containing 8–17 carbon atoms;
Z represents a bivalent radical selected from

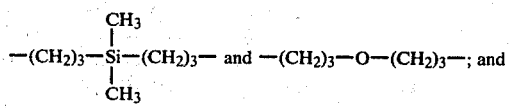

m and n represent 0 or 1.

In one preferred embodiment of the present invention, $R_1$ and $R_2$ in formula (I) above each independently represent a saturated linear alkyl containing 8–16 carbon atoms. In yet another preferred embodiment of the present invention $R_1$ and $R_2$ in formula (I) above each independently represent a saturated linear alkyl containing 8–14 carbon atoms.

These organo-silicon compounds of formula (I) exhibit good compatibility with conventional fatty bodies such as lipids and hydrocarbon oils, as well as with conventionally employed emulsifying agents, and they possess very good spreading properties on the skin and have a non-oily feel or touch.

The organo-silicon compounds of formula (I) can be provided in the form of a liquid, a powder or a wax depending on the values of $R_1$, $R_2$ and Z radicals, as well as on the values of the m and n parameters selected.

The organo-silicon compounds employed in the present invention are colorless or only slightly colored; they exhibit the advantage of being thermally and chemically stable; and they are characterized by a weak polarity, their dielectric constant being generally between 1.8 and 3 (at a frequency of 1 KHZ).

Another essential property of the organo-silicon compounds employed in the present invention, as concerns their cosmetic or pharmaceutical use, is their very weak aggressiveness towards the skin.

The organo-silicon compounds of formula (I) constitute a family of compounds which impart the above mentioned properties to compositions comprising them, totally or partially.

The judicious selection of values for $R_1$, $R_2$ and Z as well as values for the m and n parameters, permits the introduction of these organo-silicon compounds into various compositions such as milks or creams, in oil-in-water emulsions or in water-in-oil emulsions for the grooming or care of the skin, in make-up products such as lip rouge, eye shadow and eye-liners, in bath compositions, and in compositions for protection against actinic rays, such as solar oils.

The compositions of the present invention can contain the organo-silicon compounds of formula (I) either as the only component of the oily phase or in admixture with other fatty bodies principally those such as natural or synthetic oils and waxes, non-ionic, anionic, cationic or amphoteric surface active agents and principally alkyl ethers and esters of polyethylene glycol, sorbitol and polyglycerol, such as oxyethylenated fatty alcohols, oxyethylenated fatty acids, oxyethylenated sorbitan esters and soaps such as triethanolamine stearate, pigments, filters, solvents, thickening agents, preservatives, perfumes, dyes, sequestering agents, bases or acids, and also active cosmetic or pharmaceutical products.

In the compositions of the present invention, the organo-silicon compounds are generally employed in an amount, varying within large limits and depending upon the type of formulation containing the same. This concentration ranges from 1 to 100 percent, more preferably from 1 to 99.5 percent, and preferably from 3.5 to 60 percent by weight relative to the total weight of the composition.

Representative fatty bodies or material compatible with the organo-silicon compounds utilized in the compositions of the present invention which can comprise up to 90%, and preferably up to 70%, by weight of the total oily phase, include: mineral oils such as paraffin oil; treated animal oils such as cosbiol or synthetic oils such as Purcellin oil or other esters such as isopropyl palmitate or myristate; lanolin derivatives, lanolin, vegetable oils such as sweet almond oil, olive oil and avocado oil in amounts up to 5 weight percent of the total oily phase; or even synthetic triglycerides.

When the composition of the present invention contains surface active or emulsifying agents, the ratio (total fatty products:emulsifying agents) varies from 60:40 to 90:10 and preferably from 70:30 to 80:20 in accordance with the water content, as indicated below:

ratio (total fatty products):(emulsifying agent) = 90:10 for 25–80% water

| ratio (total fatty products):(emulsifying agent) | = 80:20 for 38–80% water |
| ratio (total fatty products):(emulsifying agent) | = 70:30 for 45–80% water |
| ratio (total fatty products):(emulsifying agent) | 60:40 for 55–80% water |

The emulsions can also contain a wide variety of emulsifying agents including those which are particularly compatible with the organo-silicon compounds of formula (I) such as beeswax/borax mixtures and sorbitan oleate, as well as metallic soaps.

The present invention also relates to a composition, free from all active products, the principal component of which is an organo-silicon compound of formula (I) or a mixture of these organo-silicon compounds.

This composition which is useful as a carrier or an excipient in the cosmetic or pharmaceutical industry, can be provided in the form of an oily phase alone, or in an oil-alcohol mixture, or in an oil-in-water emulsion or in a water-in-oil emulsion.

The components of this composition of the present invention, other than the organo-silicon compounds of formula (I), are principally water, lower alkanols such as ethanol, glycols such as propylene glycol, other fatty bodies or materials and emulsifying agents as well as, optionally, other conventionally employed cosmetic or pharmaceutically acceptable components or adjuvants.

The composition of the present invention contains at least one organo-silicon compound of formula (I), and optionally other fatty products and/or emulsifying agents compatible with the organo-silicon compounds of formula (I), as well as water and solvents, in accordance with the proportions indicated above.

Where the composition is provided in the form of an emulsion, it can contain the organo-silicon compound of formula (I) in an amount of 4.5 to 70, and preferably 5 to 50, percent by weight; other fatty products compatible with the organo-silicon compounds of formula (I) in an amount of 0 to 50, and preferably 3 to 32, percent by weight; an emulsifying agent compatible with the organo-silicon compounds of formula (I) in an amount of 2 to 30, and preferably 5 to 15, percent by weight; and water in an amount up to about 80 percent by weight relative to the total weight of the composition.

Where the composition of the present invention consists only of fatty materials, the organo-silicon compounds of formula (I) are present in an amount of 10 to 99.5, and preferably 10 to 60, percent by weight relative to the total weight of the composition.

Where the composition is an oil-alcohol mixture, the amount of organo-silicon compounds of formula (I) in the total mixture is at least 5 weight percent and the weight ratio, (alcohol/total composition) can vary from 30:100 to 80:100 and preferably 35:100 to 50:100. Preferably the alcohol is ethanol.

The composition of the present invention advantageously provides for a perfectly homogeneous distribution of those cosmetic and pharmaceutical active components for which it serves as excipient and it also imparts to the resulting preparation easy spreading properties and an agreeable touch or feel which is particularly desirable for topically applied compositions.

The composition of the present invention is advantageously employed as an excipient for pharmaceutical preparations for topical application to skin, as well as for cosmetic formulations, as indicated above.

The organo-silicon compounds of formula (I) can be classified into three groups, i.e.

(a) compounds wherein $n=0$, $m=0$ or 1;
(b) compounds wherein $n=1$ and $m=0$; and
(c) compounds wherein $m$ and $n=1$.

All are prepared in accordance with analogous procedures.

The organo-silicon compounds of formula (I), wherein $n=0$ and $m=0$ or 1, can be prepared by reacting a dimethyl halogeno silane with an α-olefin. The resulting dimethyl alkyl halogeno silane is then reduced, for example, with tetra aluminum hydride and lithium. The resulting alkyl dimethyl silane is then reacted with an α-olefin or also with a diallylic derivative in the presence of chloroplatinic acid as a catalyst, yielding compounds of the formula:

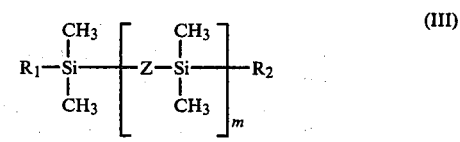

wherein $R_1$, $R_2$, $Z$ and $m$ have the meanings given above.

The organo-silicon compounds of formula (I) wherein $n=1$ and $m=0$, can be prepared by reacting a dimethyl halogeno silane with an α-olefin. The resulting dimethyl alkyl halogeno silane is converted to dimethyl alkyl silanol by the action of an alkaline base as NaOH. The resulting silanol is dehydrated, for example, in the presence of phosphoric acid to obtain finally a dialkyl tetra methyl di-siloxane.

The organo-silicon compounds of formula (I) wherein $m=1$ and $n=1$ can be prepared by reacting a dimethyl halogeno silane with a dimethyl alkyl silanol. The resulting alkyl tetramethyl disiloxane is reacted with a diallylic derivative in the presence of a catalyst such as chloroplatinic acid.

Representative organo-silicon compounds of formula (I) usefully employed in the present invention include those appearing in Table A below, and preferably, compounds Nos. $A_4$, $A_5$, $A_7$, $A_8$, $A_9$ and $A_{10}$ of this table.

Representative particularly appropriate emulsifying agents usefully employed with the organo-silicon compounds of formula (I) indicated above include polyglycerol ethers and principally polyglycerol ethers $E_1$, $E_2$ and $E_3$ whose characteristics are also indicated at the end of Table A below. Polyglycerol esters and oxyethylenated sorbitan esters can also be employed.

These polyglycerolated emulsifying agents are perfectly compatible with the organo-silicon compounds and certain binary mixtures are particularly effective. Where emulsions are provided in the form of creams, a 50:50 weight mixture of $E_1:E_2$ emulsifying agent is particularly effective. Where the emulsion is provided in the form of a milk, a 70:30 weight mixture of $E_3:E_2$ emulsifying agents is highly desirable.

TABLE A

| No. | Organo-silicon compounds useful in the invention |
|---|---|
| $A_1$ | $(CH_3)_2Si(C_{10}H_{21})_2$ |
| $A_3$ | $[(CH_3)_2Si(C_8H_{17})]_2O$ |
| $A_4$ | $[R(CH_3)_2Si]_2O$ wherein $R$ = a mixture of $-C_{12}H_{25}$ and $-C_{14}H_{29}$ |
| $A_5$ | $[C_{14}H_{29}(CH_3)_2Si]_2O$ |
| $A_7$ | $[C_{14}H_{29}(CH_3)_2Si-(CH_2)_3]_2Si(CH_3)_2$ |
| $A_8$ | $[C_{14}H_{29}(CH_3)_2Si-(CH_2)_3]_2O$ |
| $A_9$ | $[C_{14}H_{29}(CH_3)_2Si-O-Si(CH_3)_2-(CH_2)_3]Si(CH_3)_2$ |

TABLE A-continued

| No. | Organo-silicon compounds useful in the invention |
|---|---|
| $A_{10}$ | $[C_{16}H_{33}(CH_3)_2Si]_2O$ |

Emulsifying agents useful in the invention polyglycerol esters
oxyethylenated sorbitan esters
polyglycerol ethers of the formula $RO+C_2H_3O(C-H_2OH)]_{n'}H$ wherein R is a mixture of $-C_{16}H_{33}$ and $C_{18}H_{37}$, n' being a whole or decimal number having a statistical value of 2 to 6, principally polyglycerol ethers $E_1$ for which $n'=6$; $E_2$ for which $n'=2$ and $E_3$ for which $n'=4$.

The below non-limiting examples are given to provide a better understanding of the present invention. Unless otherwise stated, all parts and percentages are by weight.

Tables I, II, III and IV below, describe respectively the compositions in the form of creams, milks, oils and oil-alcohol lotions which are useful in the cosmetic industry.

Columns (1) to (10) have the following meanings:
(1) No. of the Example of the composition;
(2) Product of formula (I), designated by reference to Table A;
(3) Other fatty products or materials (FP) compatible with the products of (2);
(4) Emulsifying agents (EA) defined with reference to Table A;
(5) Sterile demineralized water;
(6) Ethyl alcohol;
(7) Various components other than those of columns (2) to (6) and present in the composition as an active component;
(8) Percent of (2) in the total fatty phase;
(9) Ratio $[(2)+(3)]:(4)$, indicated such as it appears below in columns (2) (3) and (4) and/or converted to 100 parts by weight;
(10) Types of products corresponding to the composition prepared.

Tables I and II correspond respectively to the cream and milk type compositions. In each of Examples $C_1$ to $C_8$, as well as Examples $L_1$ to $L_4$, the fatty phase can contain from 0 to 70 weight percent of a fatty material, other than the organo-silicon compound of formula (I), including, for instance, mineral oils such as paraffin oil; treated animal oil such as cosbiol; synthetic oils such as Purcellin oil; or other esters such as isopropyl palmitate or myristate; lanolin derivatives; vegetable oils such as sweet almond oil; olive oil, avocado oil; or also synthetic triglycerides.

The previously mentioned emulsifying agents and principally the polyglycerol ethers, $E_1$, $E_2$ and $E_3$ can be replaced by the following emulsifying agents: oxyethylenated fatty alcohols, known under the trade name BR1J type 56 ATLAS; oxyethylenated fatty acids, known under the trade name M1RJ type 49; oxyethylenated sorbitan esters, known under the trade name TWEEN 60; and soaps such as triethanolamine fatty acids salts like triethanolamine stearate.

Where the composition of the present invention consists essentially of an oil product and oil-alcohol lotion, the oily phase can comprise up to 75 weight percent of a fatty material other than the organo-silicon compounds of formula (I), said other fatty material being those mentioned above.

The various components in column (7) can be either products having pharmacologic activity or components used for cosmetic purposes or components for modifying the appearance or preservation characteristics of the composition.

EXAMPLE 1

Synthesis of an organo-silicon compound for use in the present invention having the formula:

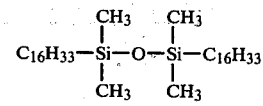

100.3 g (0.448 mole) of the $C_{16}$ alpha olefin are heated at a temperature of 110° C. 15 drops of 2% platinum hexachloride solution in methanol are then added. Subsequently, with agitation, there are added, drop by drop and slowly, 30 g (0.224 mole) of tetramethyl siloxane, the temperature of the reaction mixture being maintained between 105° and 115° C. during the addition.

Thereafter, the reaction mixture is left to stand with agitation for 2½ hours. Then the light fractions are distilled off under reduced pressure.

The above desired compound does not distill but remains in the reaction flask.

The remaining reaction mixture is filtered cold on fritted glass, and after cooling, the above compound solidifies at ambient temperature. The above compound which is in the form of a white wax has a finishing melting point of 30±2° C.

EXAMPLE 2

An emulsion containing the $C_{16}$ organo-silicon compound prepared in Example 1 is produced as follows:

| | |
|---|---|
| $C_{16}$ organo-silicon compound of Example 1 | 25 g |
| Emulsifier $E_1$ of the formula: $R-O+C_2H_3O(CH_2OH)_{\overline{6}}H$ wherein R is a mixture of $C_{16}-C_{18}$ alkyls | 4 g |
| Emulsifier $E_2$ of the formula: $R-O+C_2H_3O(CH_2OH)_{\overline{2}}H$ wherein R is a mixture of $C_{16}-C_{18}$ alkyls | 4 g |
| MPHB | 0.3 g |
| Water, sufficient for | 100 g |

The emulsifiers $E_1$ and $E_2$ are melted in a container placed in a bath thermostated at 70° C. There is then added the previously melted organo-silicon compound of Example 1.

To the resulting mixture there is added the requisite amount of water and the emulsion is formed by means of appropriate agitation.

The emulsion thus prepared is cooled to an ambient temperature of 20° C. and observed with a microscope of 100X magnification.

It is noted that the emulsion exhibits the ordinary appearance of emulsions of the oil-in-water type, i.e. a uniform and homogeneous dispersion of oil droplets in the aqueous phase.

Thus, the emulsion produced with the $C_{16}$ organo-silicon compound of Example 1 is of the same type as those prepared with the $C_{14}$ and $C_{12}$ homologues whereas, in emulsions prepared with organo-silicon compounds having $C_{18}$ and $C_{20}$ alkyl chains, these latter compounds recrystallize in the emulsions and are inappropriate for inclusion in an oil-in-water type formulation.

TABLE I

CREAMS

| (1) No. | (2) Product of Formula (I) wt % | (3) Other fatty product (FP) wt % | (4) Emulsifying Agent (EA) wt % | | (5) $H_2O^*$ wt % | (6) $C_2H_5$—OH wt % | (7) Various Active components wt % | | (8) % of (2) in the total fatty phase | (9) (2) + (3) / (4) | (10) Type of product |
|---|---|---|---|---|---|---|---|---|---|---|---|
| $C_1$ | $A_4$ 25.0 | | $E_1$ | 4.0 | | | | | | | |
| | | | $E_2$ | 4.0 | 66.7 | | MPHB 0.3 | 100 | | 25:8 | Make-up base for dry skin |
| $C_2$ | $A_4$ 15.0 | | $E_1$ | 2.5 | | | | | | | |
| | | | $E_2$ | 2.5 | 80.7 | | MPHB 0.3 | 100 | | 15:5 | Make-up base for oily skin |
| $C_3$ | $A_7$ 25.0 | | $E_1$ | 5.5 | | | | | | | |
| | | | $E_2$ | 5.5 | 63.7 | | MPHB 0.3 | 100 | | 25:11 | Day cream for dry skin |
| $C_4$ | $A_7$ 17.0 | | $E_1$ | 3.75 | | | | | | | |
| | | | $E_2$ | 3.75 | 75.2 | | MPHB 0.3 | 100 | | 17:7.5 | Day cream for oily skin |
| $C_5$ | $A_8$ 42.0 | Liquid lanolin 3.0 | $E_1$ | 5.5 | | | | | | | |
| | | | $E_2$ | 5.5 | 43.7 | | MPHB 0.3 | 42:45 = 96% | | 45:11 | Night cream |
| $C_6$ | $A_4$ 15.0 | | $E_1$ | 3.5 | | | | | | | |
| | | | $E_2$ | 3.5 | 77.7 | | MPHB 0.3 | 100 | | 15:7 | Hand cream |
| $C_7$ | $A_9$ 15.0 | | $E_1$ | 3.5 | | | | | | | |
| | | | $E_2$ | 3.5 | 77.7 | | MPHB 0.3 | 100 | | 15:7 | Eye liner cream |
| $C_8$ | $A_{10}$ 25.0 | | $E_1$ | 4.0 | 66.7 | | MPHB 0.3 | 100 | | 25:8 | Make-up base for dry skin |
| | | | $E_2$ | 4.0 | | | | | | | |

MPHB = methyl para hydroxy benzoate
\* = sterile demineralized water

TABLE II

MILKS

| (1) No. | (2) Product of Formula (I) wt % | (3) Other fatty product (FP) wt % | (4) Emulsifying Agent (EA) wt % | | (5) $H_2O^*$ wt % | (6) $C_2H_5$—OH wt % | (7) Various Active components wt % | | (8) % of (2) in the total fatty phase | (9) (2) + (3) / (4) | (10) Type of Product |
|---|---|---|---|---|---|---|---|---|---|---|---|
| $L_1$ | $A_7$ 15.0 | | $E_3$ | 4.2 | | | | | | | |
| | | | $E_2$ | 1.8 | 78.85 | | MPHB | 0.150 | 100 | 15:6 | Body milk |
| $L_2$ | $A_8$ 40.0 | | $E_3$ | 7.0 | | | | | | | |
| | | | $E_2$ | 3.0 | 49.7 | | MPHB | 0.3 | 100 | 40:20 (80:20) | Make-up remover milk for dry skin |
| $L_3$ | $A_8$ 32.0 | | $E_3$ | 5.6 | | | | | | | |
| | | | $E_2$ | 2.4 | 59.7 | | MPHB | 0.3 | 100 | 32:8 | Make-up remover milk for normal skin |
| $L_4$ | $A_8$ 24.0 | | $E_3$ | 4.2 | | | | | | | |
| | | | $E_2$ | 1.8 | 69.5 | | MPHB | 0.3 | 100 | 24:6 | Make-up remover milk for oily skin |

TABLE III

OILS\*

| (1) | (2) | (3) | | (7) | | (8) | (10) |
|---|---|---|---|---|---|---|---|
| $H_1$ | $A_4$ 45 | Olive Oil | 50 | BS | 5.0 | 45:95 = 47.5% | Solar Oil |
| $H_2$ | $A_4$ 10 | " | 85 | BS | 5.0 | 10:95 = 10.5% | " |
| $H_3$ | $A_4$ 10 | (VO-C) (IM) | 44 44 | BC | 2.0 | 10:98 = 10.2% | " |
| $H_4$ | $A_4$ 58 | (VO-C) (IM) | 20 | BC | 2.0 | 58:98 = 59.2% | " |

TABLE IV

LOTIONS

| (1) | (2) | (3) | (6) | (7) | (8) | (10) |
|---|---|---|---|---|---|---|
| OA1 | $A_4$ 10 | SFAT 36 | 50 | EHPMC 2 | 10:48 | Oil-alcohol |
| OA2 | $A_4$ 26 | SFAT 20 | 50 | EHPMC 2 | 26:48 | Oil-alcohol |
| | | Lanolin 2 | | | = 21% | lotion |
| | | Lanolin 2 | | | = 53% | lotion |

BS = butyl salicylate
BC = benzylidene camphor or derivative
VO-C = vaseline oil-codex
IM = isopropyl myristate
\*It is understood that perfumes and/or dyes can be added to these compositions.
EHPMC = ethyl hexyl p-methoxy cinnamate
SFAT = saturated $C_8$-$C_{12}$ fatty acid triglycerides
Remark:
In the compositions of Tables I, II, III and IV, the various products and principally the active products can be eliminated and the said compositions provided then as compositions capable of serving as carriers for cosmetic or pharmaceutical active products.

What is claimed is:

1. In a cosmetic or pharmaceutical composition containing an oily phase, the improvement comprising said oily phase comprising at least one organo-silicon compound having the formula

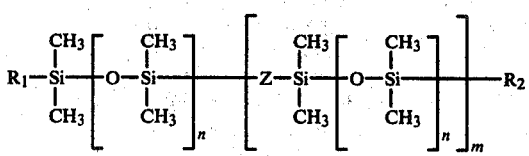

wherein
R₁ and R₂ each independently represent a saturated linear alkyl containing 8-16 carbon atoms;
Z represents a bivalent radical selected from

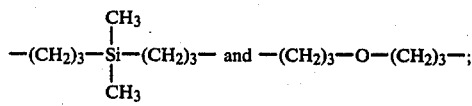

m and n each equal 0 or 1;
said compound being present in an amount ranging from 1 to 100 percent by weight relative to the total weight of said composition.

2. In a cosmetic or pharmaceutical composition containing an oily phase, the improvement comprising said oily phase comprising at least one organo-silicon compound having the formula

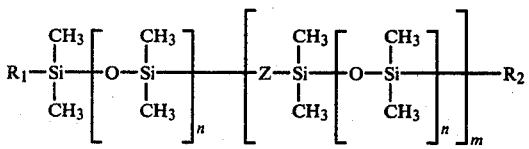

wherein
R₁ and R₂ each independently represent a saturated linear alkyl containing 8-14 carbon atoms;
Z represents a bivalent radical selected from

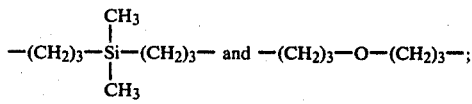

m and n each equal 0 or 1;
said compound being present in an amount ranging from 1 to 100 percent by weight relative to the total weight of said composition.

3. The composition of claim 1 which includes a fatty material other than said organo-silicon compound, said fatty material being present in an amount lower or equal to 90 percent by weight of said composition.

4. The composition of claim 1 wherein said organo-silicon compound is present in an amount between 1 and 99.5 percent by weight relative to the total weight of said composition.

5. The composition of claim 2 wherein said organo-silicon compound is present in an amount between 3.5 and 60 percent by weight relative to the total weight of said composition.

6. The composition of claim 1 in the form of an emulsion and consisting essentially of up to 80 weight percent water, 4.5-70 weight percent of said organo-silicon compound, 0-50 weight percent of a fatty material other than said organo-silicon compound, and 2-30 weight percent of an emulsifying agent.

7. The composition of claim 6 wherein water is present in an amount of 25-80 weight percent.

8. The composition of claim 1 which also includes water in an amount of 25-80 weight percent and an emulsifying agent wherein the weight ratio of total oily phase:emulsifying agent is between 90:10 and 60:40, respectively.

9. The composition of claim 8 wherein the weight ratio of total oily phase:emulsifying agent is between 80:20 and 70:30, respectively.

10. The composition of claim 8 wherein the weight ratio of total oily phase:emulsifying agent is 90:10 and the water is present in an amount of 25-80 weight percent.

11. The composition of claim 8 wherein the weight ratio of total oily phase:emulsifying agent is 80:20 and the water is present in an amount of 38-80 weight percent.

12. The composition of claim 8 wherein the weight ratio of total oily phase:emulsifying agent is 70:30 and the water is present in an amount of 45-80 weight percent.

13. The composition of claim 8 wherein the weight ratio of total oily phase:emulsifying agent is 60:40 and the water is present in an amount of 55-80 weight percent.

14. The composition of claim 8 wherein said emulsifying agent is selected from a polyglycerol ester, an oxyethylenated sorbitan ester, a polyglycerol ether of the formula RO₊C₂H₃O(CH₂OH)]ₙ'H wherein R is a mixture of —C₁₆H₃₃ and —C₁₈H₃₇, n' is a whole or decimal number having a statistical value of 2 to 6, an oxyethylenated fatty alcohol, an oxyethylenated fatty acid and triethanolamine fatty acids salts.

15. The composition of claim 14 wherein said emulsifying agent has the formula

RO₊C₂H₃O(CH₂OH)]ₙ'H wherein R is a mixture of —C₁₆H₃₃ and —C₁₈H₃₇ and n' is a whole or decimal number having a statistical value from 2 to 6.

16. The composition of claim 15 wherein n' has a statistical value selected from 2, 4 and 6.

17. The composition of claim 1 wherein the cosmetic composition consists only of said oily phase and wherein said organo-silicon compound is present in an amount ranging from 10 to 99.5 percent by weight thereof, the remainder being another fatty material.

18. The composition of claim 17 wherein said organo-silicon compound is present in an amount ranging from 10 to 60 percent by weight thereof.

19. The composition of claim 17 wherein said fatty material other than said organo-silicon compound is selected from a mineral oil, a treated animal oil, a vegetable oil, a fatty ester, lanolin derivative, synthetic oil and a synthetic triglyceride.

20. The composition of claim 1 which is an oil-alcohol mixture wherein said organo-silicon compound is present in an amount of at least 5 weight percent of said mixture and said alcohol is present in an amount such that the weight ratio of alcohol:total composition ranges from 30:100 to 80:100.

21. The composition of claim 20 wherein the weight ratio of alcohol:total composition ranges from 35:100 to 50:100.

22. The composition of claim 20 wherein the alcohol is ethanol.

23. The composition of claim 1 wherein said organo-silicon compound is selected from
  (a) $[R(CH_3)_2Si]_2O$ wherein R is a mixture of $-C_{12}H_{25}$ and $-C_{14}H_{29}$,
  (b) $[C_{14}H_{29}(CH_3)_2Si(CH_2)_3]_2Si(CH_3)_2$,
  (c) $[C_{14}H_{29}(CH_3)_2Si(CH_2)_3]_2O$,
  (d) $[C_{14}H_{29}(CH_3)_2Si-O-Si(CH_3)_2-(CH_2)_3]_2Si(CH_3)_2$, and
  (e) $[C_{16}H_{33}(CH_3)_2Si]_2O$.

24. The composition of claim 6 wherein said oily phase is an organo-silicon compound of the formula $[C_{14}H_{29}(CH_3)_2Si]_2O$ and said emulsifying agent is a mixture of a polyglycerol ether of the formula $R-O+C_2H_3O(CH_2OH)]_4H$ wherein R is a mixture of $C_{16}$ and $C_{18}$ alkyl radicals and a polyglycerol ether of the formula $R-O+C_2H_3O(CH_2OH)]_2H$ wherein R is a mixture of $C_{16}$ and $C_{18}$ alkyl radicals.

* * * * *